United States Patent [19]

Kaelble

[11] 4,123,409

[45] Oct. 31, 1978

[54] SEALING MATERIAL FOR USE IN CONTACT WITH ANIMAL TISSUE

[75] Inventor: David H. Kaelble, Thousand Oaks, Calif.

[73] Assignee: Rockwell International Corporation, El Segundo, Calif.

[21] Appl. No.: 774,297

[22] Filed: Mar. 4, 1977

[51] Int. Cl.$^2$ .............................................. C08L 83/10
[52] U.S. Cl. .................... 260/29.1 SB; 260/33.6 AQ; 128/1 R
[58] Field of Search ................ 260/29.1 SB, 33.6 AQ, 260/33.6 A, 827; 128/1 R, 132 R, 260, 294

[56] References Cited

U.S. PATENT DOCUMENTS

| | | | |
|---|---|---|---|
| 3,100,488 | 8/1963 | Orowan | 128/283 |
| 3,373,745 | 3/1968 | Benfield et al. | 128/283 |
| 3,612,053 | 10/1971 | Pratt | 128/283 |
| 3,665,052 | 5/1972 | Saam et al. | 260/827 |
| 3,676,387 | 7/1972 | Lindlof | 260/28.5 B |
| 3,827,999 | 8/1974 | Crossland | 260/33.6 AQ |
| 3,932,327 | 1/1976 | Naylor | 260/33.6 A |
| 3,964,485 | 6/1976 | Neumeier | 128/283 |
| 4,000,836 | 1/1977 | Williams et al. | 260/29.1 SB |

OTHER PUBLICATIONS

Morton-Rubber Technology (2nd ed.) (Van Nostrand) (N.Y.) (1973), p. 530.
Hackhi's Chemical Dictionary (4th ed.) (McGraw-Hill) (N.Y.) (1969), p. 431.

*Primary Examiner*—Lewis T. Jacobs
*Attorney, Agent, or Firm*—L. Lee Humphries; Craig O. Malin

[57] ABSTRACT

A sealing material for use in contact with animal tissue such as for sealing a stoma opening. The material is a thermoplastic elastomer made by mixing: (1) at least one part of a high molecular weight, nonvolatile oil with (2) a block copolymer having non-elastomeric thermoplastic end blocks and an elastomeric intermediate block which form separate phases. In one embodiment, the end blocks are polystyrene, the intermediate block is either butadiene or isoprene polymer, and the oil is a hydrocarbon oil. In another embodiment, the end blocks are polyalphamethylstyrene, the intermediate block is polydimethylsiloxane, and the oil is a silicone oil.

2 Claims, No Drawings

4,123,409

SEALING MATERIAL FOR USE IN CONTACT WITH ANIMAL TISSUE

BACKGROUND OF THE INVENTION

A. Field of the Invention

This application relates to the field of seals and prophylactics; and particularly to the field of seals for post-surgical devices such as ostomy devices, and prophylactic devices used in contact with animal tissue.

B. Description of the Prior Art

Materials used in contact with animal tissue require a unique combination of properties. Generally, they must be soft and flexible so as to readily conform to the shape of the tissue without irritation. Frequently, the materials must have a certain "feel" and provide strength and ready release (low tack) such as in the case of surgical gloves and other prophylactic devices. When used as seals, the materials must intimately engage the skin or tissue to prevent leakage of the materials being sealed. The numerous plastics, rubbers, and natural materials do not possess all the optimum properties for use in the many applications in contact with animal tissue, and consequently there is a continuing need for improved materials in these applications.

For example, surgical procedures (for example colostomy, circumostomy, cutaneous ureterostomy, and ileostomy) have been developed which create an opening in internal organs which opening extends through the patient's skin, generally in the form of a stubby protrusion or stoma. Various body material such as fecal material and urine must regularly pass through the stoma out of the body into the external environment. Post-surgical patients having such operations must therefore wear bags to contain these bodily excretions.

Because of the obnoxious nature of these bodily excretions, it is important that there be a good seal between the stoma and the bag worn by the patient. Numerous enterostomy appliances are available for holding a bag in sealing engagement with the body of a patient. A critical element of all these devices is the sealing device or material which contacts the living tissues such as the skin and stoma of the patient. Such sealing device must be comfortable, reliable, non-irritable, sanitary, and easily held in place for long periods of time. Of prime importance is that the sealing device must be liquid and gas tight, and odorproof.

The sealing device can take the form of a simple washer-type gasket as described in U.S. Pat. No. 3,980,084 or a more complicated molded part such as described in U.S. Pat. No. 3,964,485. In all cases, however, a difficult sealing problem is encountered because of the stretching of the skin during normal body motion and the requirement that the seal be non-irritating and convenient to apply and remove.

A common ostomy sealing material is a gelatinous mixture of Karaya gum or other natural gums and glycerol. This mixture is water soluble and is a nutrient which is capable of supporting bacterial growth. Additionally, Karaya gels have limited shelf life and harden after storage for extended periods under ambient conditions.

Synthetic materials such as soft plastics, rubber, adhesives, fabric pads, and even metals have been tried with various degrees of success. Some of these materials are hard and uncomfortable, others require excessive pressure to provide a tight joint, and some adhere to the skin and are difficult to remove.

SUMMARY OF THE INVENTION

It is an object of the invention to provide an improved sealing material for use in contact with living tissue.

It is an object of the invention to provide a strong yet highly flexible material which readily conforms to the skin of a person.

It is an object of the invention to provide a sealing material which has a compliant, wetting-type action when placed against the objects being sealed.

It is an object of the invention to provide a material which will produce a resilient airtight seal under substantially zero pressure, or at least only a light pressure.

It is an object of the invention to provide a material which will adhere to the surface of an object and yet require only a light force to remove it from the surface.

It is an object of the invention to provide a material for use in sealing enterostomy devices to the body of a patient without requiring adhesives.

It is an object of the invention to provide an improved seal for use in contact with animal tissue.

It is an object of the invention to provide an improved prophylactic sealing material.

According to the invention, a thermoplastic elastomer sealing material is made by mixing: (1) at least one part of a high molecular weight, nonvolatile oil with (2) a block copolymer having non-elastomeric thermoplastic end blocks, and an elastomeric intermediate block which form separate phases. In one embodiment, the end blocks are polystyrene, the intermediate block is either butadiene or isoprene polymer, and the oil is a hydrocarbon oil. In another embodiment, the end blocks are polyalphamethylstyrene, the intermediate block is polydimethylsiloxane, and the oil is a silicone oil.

DESCRIPTION OF THE PREFERRED EMBODIMENT

The above objects and advantages are achieved, according to the invention, by the provision of a thermoplastic elastomer obtained by mixing a block copolymer with a high molecular weight nonvolatile oil. The resulting thermoplastic elastomer has the desired characteristics of strength and resistance to tearing, high flexibility and conformability to skin or to a part surface, and good wetting action of the elastomer to the surface. The soft compliant elastomer readily conforms to any shaped surface, including rough and irregular surfaces, and also has the unique characteristic of wetting the surface to eliminate voids and air pockets while providing a good airtight seal, simply by applying the elastomer to the surface with substantially no application of external forces, or simply by its own weight, and permitting its removal by a similar very small force, the elastomer maintaining a relatively stable shape and leaving no residue on debonding.

The essential polymer component of the mixture employed in producing the elastomer material or composition of the invention is a thermoplastic rubber polymer which does not require vulcanization or curing. Polymers of this type differ fundamentally in structure from the typical plastic or rubber homopolymers or random copolymers, which generally do require vulcanization or curing. The polymers employed according to the present invention are block copolymers having the general formula $$(A - B)_n - A \quad n \leq 1.0$$

where each A is a non-elastomeric thermoplastic end block having a glass transition temperature above room temperature, i.e., above about 25° C., and B is an elastomeric polymer intermediate block having a glass transition temperature below room temperature, usually below about 10° C., the end blocks A and the intermediate block having molecular weights as more specifically defined below.

The term "block" copolymer is meant to denote polymeric chains containing alternating blocks of polymers, each block differing materially from the next adjacent block. Examples of block copolymers applicable to the present invention include: Shell's Kraton 1101 and Kraton 1102 (A = polystyrene and B = 1,4 polybutadiene), Kraton 1107 (A = polystyrene and B = polyisoprene), Kraton G (A = polystyrene and B = polyethylene-propylene copolymer), Dow Corning X4-2516 lot 114 (A = polyalphamethylstyrene and B = polydimethylsiloxane) and AMOCO's Resin 18 (A = polystyrene and B = polyisoprene). The development of block copolymers or thermoplastic elastomers is an active field with new materials being currently introduced. Some such block copolymers expected to have application according to the present invention and known now by their tradename include Uniroyals's TPR, Shell's Elexar, DuPont's Hytrel and Somel, and B. F. Goodrich's Telcar.

The above unvulcanized block copolymers have individual chains consisting of three or more blocks, the elastomeric intermediate block, and a thermoplastic block on each end. Since the end blocks and the elastomeric intermediate blocks are mutually incompatible, the bulk polymer separates into two microphase regions, the block A phase and the block B phase. Where the thermoplastic end blocks are in minor proportion, as employed in the present invention and as noted more fully below, such end blocks associate together to form discrete particles, such particles acting as cross-links for the elastomeric intermediate block. The resulting network is thus held together by reversible physical bonds in contrast to the permanent chemical bonds characteristic of vulcanized or cured elastomers. Under these conditions, the end blocks coalesce when cast from a solvent or congeal when cooled from a melt to form sub-microscopic particles. These particles, held together by van der Waals forces, form a discrete phase while the elastomeric mid-blocks form a continuous phase. Each individual molecule thus has its end blocks in one of the many particles and its intermediate block in the continuous elastomer phase.

For purposes of the present invention, the minimum average molecular weight of each end block is about 5,000, the average molecular weight of each such end block ranging from about 5,000 to about 50,000, so that the minimum total average molecular weight of both end blocks is about 10,000, the total average molecular weight of both end blocks ranging from about 10,000 to about 100,000. The minimum average molecular weight of the intermediate or mid-block is about 25,000 the average molecular weight of such intermediate block ranging from about 25,000 to about 500,000, the preferred average molecular weight range of such intermediate block ranging from about 25,000 to about 200,000.

Thus, the total average molecular weight of the block copolymers employed according to the invention ranges from about 35,000 to about 600,000, preferably between about 35,000 and about 300,000. Of particular significance, it is essential for obtaining the advantageous properties of the invention that the sum of the average molecular weight of both end blocks be not in excess of 35% of the total average molecular weight of the block copolymer.

In a preferred first embodiment, the non-elastomeric thermoplastic end blocks are styrene and the elastomeric polymer intermediate block is selected from the group consisting of butadiene and isoprene polymer blocks. Such styrene-butadiene and styrene-isoprene block copolymers and their method of preparations are described in U.S. Pat. No. 3,265,765. Specific examples of such block copolymers which can be employed in producing the elastomer composition of the invention are the thermoplastic rubber copolymers which can be employed in producing the elastomer composition of the invention are the thermoplastic rubber polymers marketed as Kraton 1101 and 1102, which are block copolymers of styrene-butadiene. Each polystyrene end block has an average molecular weight of about 9,500 to 11,000 and the polybutadiene intermediate block has an average molecular weight of about 37,500 to 54,000, the total average molecular weight of such block copolymer being about 56,500 to 76,000. The material marketed as Kraton 1107 is a styreneisoprene block copolymer, each polystyrene end block of which has an approximate average molecular weight of about 8,000 to 12,000. The polyisoprene intermediate block has an average molecular weight of about 34,000 to 60,000, the total average molecular weight of Kraton 1107 copolymer being about 50,000 to 84,000. These Kraton 1101, 1102 and 1107 block copolymers are marketed by Shell Chemical Company.

Typical physical properties of these copolymers at 23° C. are noted in Table 1 below.

TABLE 1

|  | KRATON 1101 KRATON 1102 | KRATON 1107 |
|---|---|---|
| Tensile Strength ($T_B$), psi | 4600 | 3100 |
| 300% Modulus ($M_{300}$), psi | 400 | 100 |
| Elongation ($E_B$), % | 880 | 1300 |
| Angle Tear Strength (ASTM Method D624), pli | 190 | 120 |

These materials are marketed in the form of white crumbs having a specific gravity of 0.93 to 0.94.

The elastomer material produced according to the invention employing the styrene-isoprene block copolymer such as Kraton 1107, is substantially softer and of lower strength and modulus as compared to the elastomer produced employing the styrene-butadiene block copolymer.

If desired, mixtures of the styrene-butadiene and styreneisoprene copolymers can be employed, e.g. a mixture of Kraton 1101 and Kraton 1107.

Also, if desired, the block copolymer employed in the invention composition, such as the "Kraton" copolymers noted above, can contain stabilizers and antioxidants, such as 2,6 di-tert-butyl-4-methyl phenol, as well as additives for protection of the block copolymer component against ultraviolet radiation.

The second essential component of the mixture employed for producing the elastomeric material of the invention according to the first embodiment is a hydrocarbon oil which is compatible and associates with the elastomeric polybutadiene or polyisoprene intermediate block or intermediate block phase of the above block copolymer, but is incompatible with the thermoplastic polystyrene end blocks or end block phase. The result is the production of an elastomer material according to the invention having extremely high compliance combined with high wettability, while still retaining high resiliency, extensibility and strength. A preferred oil for this purpose is mineral oil, e.g. having a viscosity at ambient temperature of about 5 to about 1,000 centistokes. Such mineral oil is preferably a low aromatic content, and is essentially aliphatic in nature, such oil having an average molecular weight, e.g. ranging from about 250 to about 1,000 and having low pour point, that is less than about 32° F.

An alternative oil which can be employed in place of mineral oil is liquid polybutadiene, e.g. having an average molecular weight ranging from about 2,000 to about 10,000. Mineral oil has the advantage over polybutadiene of being resistant to oxidation over a relatively extended period of time, whereas liquid polybutadiene is more susceptible to oxidation. Liquid polybutadiene, on the other hand, has the advantage over mineral oil of having a lower vapor pressure as compared to mineral oil, so that volatilization of the liquid polybutadiene is substantially negligible.

It is essential for purposes of the invention that the block copolymer component, that is the styrene-butadiene or styrene-isoprene block copolymer, be employed in a weight ratio with respect to the oil, preferably mineral oil, of 1 part of the block copolymer to at least 1 part of the oil. Generally, the ratio of proportions of block copolymer to oil ranges from 1 part of block copolymer to 2 parts of the oil, to 1 part of block copolymer to 15 parts oil, by weight. The preferred range is from 1 part of the block copolymer to 2 parts of the oil, to 1 part of the block copolymer to 10 parts of the oil, by weight. An optimum ratio is 1 part of block copolymer, e.g. styrene-butadiene copolymer, to 2.5 parts of oil, e.g. mineral oil, by weight.

Within the above-noted scope of proportions of block copolymer to oil, such copolymer and oil have the characteristics of clathrate compounds, also known as inclusion complexes, in which the molecules of the oil are substantially completely caged within the molecular structure of the block copolymer. That is, the block copolymer forms a lattice structure or compartments in which the oil, e.g. mineral oil, is held, and does not bleed out. Under these conditions, and within the ranges of proportions of block copolymer to oil noted above, the resulting elastomer according to the invention has high compliance and good wettability characteristics. On the other hand, if for example only 1 to 0.5 parts or less of oil is employed per part of block copolymer, the oil functions simply as a plasticizer, and the resulting elastomer has substantially reduced compliance and essentially no wettability characteristics, and hence will not have the properties of forming an effective seal.

In a preferred second embodiment, the non-elastomeric thermoplastic end blocks A are polyalphaphamethylstyrene and the elastomeric polymer intermediate block B is polydimethyl siloxane. A specific example of such a block copolymer which can be employed in producing the elastomer composition of the invention is commercially identified as Dow Corning X4-2516, lot 114. A preferred oil for admixing with Dow Corning block copolymer of this second embodiment is a silicone oil marketed as DC200 and having a viscosity of 1 to 1000 centistokes at ambient conditions. As in the first embodiment, it is important that the ratio of block copolymer to oil be at least 1 part copolymer to 1 part oil.

The mixing of the oil and block copolymer can be accomplished by heating and mechanical working in conventional thermoplastic forming processes. Alternatively, a temporary volatile solvent for both oil and block copolymer can be employed to produce a molecular mixing at room temperature with minor mechanical agitation. Removal of the solvent by evaporation from a cast film or coating causes the segregation of the oil to the elastomer B phase and the formation of physical crosslinks by the glassy A phase. Examples of suitable solvents for this purpose are toluene, benzene, m-, p-, or o-xylene, and cyclohexane, or blends of such solvents such as a blend of toluene and one or more of the above-noted xylenes, or a mixture of the three xylene isomers as in commercial xylene.

Such solvents should be employed in a proportion ranging from about 20 to about 75%, preferably about 40 to about 60%, by weight of the total mixture or composition. The solvents employed as noted above and the amounts thereof are utilized so that the solvent dissolves both the polystyrene domains or phase of the block copolymer as well as the rubber network, that is the polybutadiene or polyisoprene phase. Such solvents should also be compatible with and dissolve the oil, e.g. mineral oil or silicone oil.

In providing the mixture for producing the elastomer material of the invention, the oil is poured over the block copolymer which can be in the form of crumbs or particles, employing the proportions of oil with respect to block copolymer within the ranges noted above. The mixture of block copolymer and oil is permitted to stand under ambient conditions until the crumbs or particles of the block copolymer absorb substantially all of the oil, usually requiring several hours, e.g. from about 1 to about 5 hours. Then the solvent is added to the resulting mixture, and the composition is permitted to stand at ambient temperatures for a period of time, for example about 24 hours.

At this point the resulting composition is substantially in the form of a thick syrup and is stirred to maintain the composition homogeneous. Such mixture can be stored with remaining solvent contained therein, or following evaporation of substantially all of the solvent, the resulting composition can be placed in an enclosed container and will form a viscous mass or solution upon standing.

In final processing for production of an elastomer material according to the invention, the composition preferably is placed in a vacuum oven to remove all entrapped air and any remaining solvent. It is noted that such solvent should be removed or driven off at temperatures not in excess of about 400° F., e.g. at a temperature ranging from about 275° to about 390° F. At a temperature of about 390° F. evaporation of solvent can be accomplished usually in a relatively short time of a matter of minutes, e.g. about 5 to about 6 minutes. If the solvent is removed at temperature above about 400° F., or for longer periods at somewhat lower temperatures of say about 390° F., the resulting elastomeric product is inferior because under these conditions the oil is driven out of the composition by vaporization. It is essential that such oil be retained in the elastomeric product to obtain a thermoplastic elastomer having the advantageous properties according to the invention.

Following removal of air and solvent, the composition is generally heated at temperatures below the above-noted temperature of 400° F., sufficient to permit the thermoplastic composition to be injection molded or to be processed by conventional extrusion processing techniques.

The resulting thermoplastic rubber elastomer, as noted above, retains substantially all of the oil and the elastomer product has high flexibility and is highly compliant, while having excellent strength and toughness. In addition, and of particular significance, the resulting elastomer possesses the above-noted thixotropic-like properties which permits the elastomer to wet the surface of an object and expel the interfacial air layer and avoid air pockets. Thus, the elastomer can be readily applied to the skin or other tissue such as a stoma of the patient substantially without the application of external forces, that is by employing extremely low pressures, e.g. less than 0.1 psi for this purpose, while also requiring only minimal force for removal of the elastomer. Thus, the elastomer possesses both easy bonding and easy release characteristics and bonds like pressure sensitive adhesive but can be removed with the same small force required in the initial bonding, whereas pressure sensitive adhesive requires an essentially greater force for release than for bonding. The thixotropic-like action is retained by the elastomer over a wide temperature range of from about −22° F. up to about 115° F.

The following are examples of practice of the invention, the amounts being expressed in terms of parts by weight unless otherwise indicated.

EXAMPLE 1

Ten parts of the styrene-butadiene block copolymer, Kraton 1101 crumbs having the molecular weight characteristics noted above, is mixed with 25 parts of mineral oil of low aromatic content, having a viscosity of about 5 to 10 centistokes at ambient temperature, and a molecular weight of about 500. In this mixing procedure, the mineral oil is poured over the Kraton 1101 block copolymer crumbs, and the mixture of block copolymer crumbs and oil is permitted to stand under ambient conditions for a period of about 2½ hours until such crumbs have absorbed substantially all of the oil.

To the resulting block copolymer-mineral oil mixture is added 35 parts of toluene. The resulting composition is permitted to stand at ambient temperature for about 24 hours. During this period, a portion of the toluene solvent is evaporated.

Following the above-noted period, the resulting composition is substantially in the form of a thick syrup and is stirred to maintain the composition in the form of a homogeneous mass.

The composition is then placed in a vacuum oven at a temperature of about 390° F., for a period of about 5 minutes, thus removing the remainder of the solvent, without removal of any of the mineral oil and without causing the mineral oil to burn. The composition is then removed from the vaccum oven and formed into thermoplastic seals by injection molding. The resulting elastomer seals are observed to be highly flexible and compliant, and when applied to human skin readily wet the skin and adhere thereto without any force. Following application, such elastomer is readily removed by a very slight peeling action.

EXAMPLE 2

The procedure of Example 1 is substantially repeated except that a polyalphamethylstyrene — polydimethylsiloxane block copolymer (Dow Corning X4-2516, lot 114) is used with silicone oil (DC 200) in the ratio of 1 to 2, respectively. The mixture is processed with 5 part of toluene as a temporary solvent. After removal of the solvent in accordance with Example 1, a highly flexible elastomer is formed having similar properties as the elastomer produced in Example 1.

EXAMPLES 3–10

Elastomer mixtures corresponding to those listed in the table below are prepared according to the procedure of Example 1. In these examples the mineral oil and silicone oil are same oils as employed in Example 1.

TABLE 2

| | EXAMPLES (parts by weight) | | | | | | | |
|---|---|---|---|---|---|---|---|---|
| | 3 | 4 | 5 | 6 | 7 | 8 | 9 | 10 |
| Kraton 1101 | 25 | 10 | 10 | 10 | — | — | — | — |
| Kraton 1107 | — | — | — | — | 10 | — | — | — |
| Mineral Oil | 50 | 30 | 50 | 70 | 25 | — | — | — |
| Toluene | 70 | 20 | 80 | 90 | 35 | 50 | 60 | 70 |
| X4-2516 | — | — | — | — | — | 10 | 10 | 10 |
| Silicone Oil | — | — | — | — | — | 10 | 30 | 70 |

Upon injection molding of the respective elastomer compositions of each of Examples 3–10, in each case a highly flexible and compliant thermoplastic elastomer is formed having good strength and extensibility, and having thixotropic-like properties of wettability.

EXAMPLE 11

The procedure of Example 1 is repeated but employing in place of mineral oil, the same amount of liquid polybutadiene having an average molecular weight of about 5,000, and utilizing as solvent, in place of toluene, the same amount of a commercial mixture of xylenes, including o-, m- and p-xylenes.

The resulting thermoplastic elastomer is highly flexible and compliant, of good strength, and has thixotropic-like wettable properties similar to the elastomer of Example 1.

From the foregoing, it is seen that the invention provides a novel body sealing and prophylactic material which has unexpected and advantageous properties including high conformability to skin and thixotropic-like or wettable characteristics permitting good adherence to living animal tissue without application of external pressure, as well as easy removal therefrom as desired.

Numerous variations and modifications may be made without departing from the present invention. Accordingly, it should be clearly understood that the form of the present invention described above is illustrative only and is not intended to limit the scope of the present invention.

What is claimed is:

1. A method of fabricating a prophylactic device for use in contact with living animal tissue, comprising the steps of:

providing a block copolymer having the general formula $$(A - B)_n - A \quad n \geq 1.0$$

wherein A is a non-elastomeric thermoplastic polyalphamethylstyrene end block and B is an elastomeric polydimethylsiloxane intermediate block, said blocks forming separate phases A and B, said end blocks A each having a minimum average molecular weight of about 5,000, said elastomeric intermediate block B having a minimum average molecular weight of about 25,000, said block copolymer having an average molecular weight ranging from about 35,000 to about 600,000, the sum of the average molecular weights of both end blocks A being not in excess of 35% of the total average molecular weight of said block copolymer;

admixing a high molecular weight nonvolatile silicone oil in the weight ratio 1 part of said block copolymer to at least 1 part of said oil, said oil being selectively dissolved in said elastomeric intermediate block B phase of said block copolymer; and forming the mixture into said prophylactic device for use in contacting living animal tissue.

2. A method of fabricating an ostomy seal for use in providing a seal between the skin around the stomal opening and a post-surgical drainage pouch comprising:

providing a block copolymer having the general formula $$(A - B)_n - A \quad n \geq 1.0$$

wherein each A is a non-elastomeric thermoplastic polyalphamethylstyrene end block and B is an elastomeric polydimethylsiloxane intermediate block, said blocks forming separate phases A and B, said end blocks A each having a minimum average molecular weight of about 5,000, said elastomeric intermediate block B having a minimum average molecular weight of about 25,000, said block copolymer having an average molecular weight ranging from about 35,000 to about 600,000, the sum of the average molecular weights of both end blocks A being not in excess of 35% of the total average molecular weight of said block copolymer;

admixing a high molecular weight nonvolatile silicone oil in the weight ratio 1 part of said block copolymer to at least 1 part of said oil, said oil being selectively dissolved in said elastomeric intermediate block B phase of said block copolymer; and forming the mixture into said ostomy seal.

* * * * *